United States Patent
Hasler et al.

(10) Patent No.: US 7,150,730 B2
(45) Date of Patent: *Dec. 19, 2006

(54) REFASTENABLE PANT-LIKE DISPOSABLE UNDERGARMENT

(75) Inventors: Paul Wendel Hasler, Appleton, WI (US); Suzanne Marie Schmoker, Oshkosh, WI (US); Jeffery Michael Tabor, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 383 days.

This patent is subject to a terminal disclaimer.

(21) Appl. No.: 10/791,623

(22) Filed: Mar. 1, 2004

(65) Prior Publication Data

US 2005/0192553 A1    Sep. 1, 2005

(51) Int. Cl.
*A61F 13/20* (2006.01)
(52) U.S. Cl. ............... 604/385.11; 604/385.01; 604/387; 604/389; 604/391; 604/394
(58) Field of Classification Search .......... 604/385.03, 604/385.11, 386, 396, 391, 389, 385.01, 395
See application file for complete search history.

(56) References Cited

U.S. PATENT DOCUMENTS

| | | | |
|---|---|---|---|
| 5,137,525 A * | 8/1992 | Glassman | 604/385.11 |
| 5,163,932 A | 11/1992 | Nomura et al. | |
| 5,624,420 A * | 4/1997 | Bridges et al. | 604/365 |
| 5,624,428 A | 4/1997 | Sauer | |
| 5,989,236 A | 11/1999 | Roe et al. | |
| 5,997,521 A | 12/1999 | Robles et al. | |
| 6,113,717 A | 9/2000 | Vogt et al. | |
| 6,287,287 B1 | 9/2001 | Elsberg | |
| 6,302,871 B1 | 10/2001 | Nakao et al. | |
| 6,352,528 B1 | 3/2002 | Weber et al. | |
| 6,443,940 B1 | 9/2002 | Ashton et al. | |
| 6,447,497 B1 | 9/2002 | Olson | |
| 6,454,751 B1 | 9/2002 | Olson | |
| 6,497,695 B1 | 12/2002 | Bruemmer-Prestley et al. | |
| 6,500,161 B1 | 12/2002 | Freiburger et al. | |
| 6,508,797 B1 | 1/2003 | Pozniak et al. | |
| 6,514,235 B1 | 2/2003 | Freiburger et al. | |
| 6,572,601 B1 | 6/2003 | Suprise et al. | |
| 6,575,953 B1 | 6/2003 | Olson | |

(Continued)

FOREIGN PATENT DOCUMENTS

EP    0 839 507 A1    5/1998

(Continued)

*Primary Examiner*—Jacqueline F. Stephens
(74) *Attorney, Agent, or Firm*—Thomas J. Connelly

(57) ABSTRACT

A refastenable pant-like disposable undergarment for absorbing human discharge is disclosed. The undergarment includes a front panel, a back panel, and an absorbent assembly secured therebetween. The front and back panels are joined together to form a waist opening and a pair of leg openings. A pair of tear lines is formed in the front panel with each extending from the waist opening to one of the respective leg openings. A pair of attachment members is secured across the pair of tear lines and one side of the attachment members is removeably fastened to the front panel. The undergarment further includes a pair of ear flaps formed in the front panel under the pair of attachment members. Each ear flap extends to a portion of one of the pair of tear lines and is fixed to one of the attachment members. As the attachment members are opened, the pair of ear flaps will cause the pair of tear lines to break.

20 Claims, 4 Drawing Sheets

U.S. PATENT DOCUMENTS

| | | |
|---|---|---|
| 6,579,275 B1 | 6/2003 | Pozniak et al. |
| 6,752,796 B1 | 6/2004 | Karami |
| 6,849,067 B1 * | 2/2005 | Fletcher et al. ............. 604/389 |
| 2003/0055389 A1 * | 3/2003 | Sanders et al. ............. 604/358 |
| 2003/0135192 A1 * | 7/2003 | Guralski et al. ............ 604/391 |
| 2004/0186451 A1 * | 9/2004 | Bishop et al. ......... 604/385.11 |

FOREIGN PATENT DOCUMENTS

| | | |
|---|---|---|
| EP | 1 009 347 B1 | 11/2002 |
| EP | 1 297 808 A2 | 4/2003 |
| EP | 1 009 350 B1 | 5/2003 |
| WO | WO 98/53780 A1 | 12/1998 |
| WO | WO 99/11211 A1 | 3/1999 |
| WO | WO 99/60966 A1 | 12/1999 |
| WO | WO 99/60971 A1 | 12/1999 |
| WO | WO 00/35396 A1 | 6/2000 |
| WO | WO 00/37010 A1 | 6/2000 |
| WO | WO 2002/069864 A2 | 9/2002 |
| WO | WO 2002/076364 A1 | 10/2002 |
| WO | WO 2002/079360 A1 | 10/2002 |
| WO | WO 2002/083050 A1 | 10/2002 |
| WO | WO 2002/083078 A2 | 10/2002 |
| WO | WO 2003/024372 A2 | 3/2003 |
| WO | WO 2003/024375 A2 | 3/2003 |
| WO | WO 2003/024377 A2 | 3/2003 |

\* cited by examiner

REFASTENABLE PANT-LIKE DISPOSABLE UNDERGARMENT

BACKGROUND OF THE INVENTION

Pant-like disposable undergarments for absorbing human discharges can appear similar in size and shape to regular cloth underwear which is designed to be laundered and reused two or more times. A disposable undergarment is an article intended to be worn by persons, including infants, toddlers, or adults, that is designed for single use or temporary use and is meant to be disposed of after being used once instead of being laundered or dry cleaned for re-use. Some examples of disposable undergarments include infant diapers, training pants, adult incontinence garments, feminine pants, etc.

Some pant-like disposable undergarments manufactured today resemble regular cloth underwear in that they have a waist opening and a pair of leg openings. Such pant-like disposable undergarments can be pulled up around the torso of a user in a similar fashion as regular cloth underwear. Still other pant-like disposable undergarments contain an attachment mechanism that will allow the undergarment to be opened into a flat configuration prior to being placed around the torso of a user. This design is beneficial for bed bound users who may be immobile and who need assistance in securing the undergarment in place. Still other refastenable, pant-like undergarments contain attachment means for opening and closing the waist opening after the undergarment has been positioned around the torso of a user. This feature is advantageous in that the user does not have to undress when there is a desire to check the status of the undergarment. One refastenable, pant-like disposable undergarment currently being commercially sold by Kimberly-Clark Corporation uses a pair of tear lines with each extending from the waist opening to one of the leg openings. The tear lines are designed to be broken either prior to positioning the undergarment around the user's torso or while the undergarment is already positioned about the user's torso. A pair of attachment members is then utilized to refasten the undergarment so that it is snug about the user's torso.

It has been found that a portion of each of the tear lines is visually hidden by the attachment members and some users cannot see them and thereby do not know that they are present. Second, each tear line may be ergonomically hard to tear open by older adults, some of who may be suffering from arthritis.

Now a refastenable, pant-like disposable undergarment for absorbing human discharge has been invented that uses a pair of ear flaps, each formed adjacent to one of the pair of tear lines, which will cause the tear lines to break as the attachment members are opened.

SUMMARY OF THE INVENTION

Briefly, this invention relates to a refastenable pant-like disposable undergarment for absorbing human discharge. The refastenable pant-like disposable undergarment includes a front panel, a back panel, and an absorbent assembly secured to the front and back panels. The front and back panels are joined together by a pair of seams to form a waist opening and a pair of leg openings. The undergarment also includes a pair of tear lines formed in the front panel with each extending from the waist opening to one of the respective leg openings. A pair of attachment members, each having a first region and a second region, is secured to the undergarment such that each of the first regions is secured to one side of each of the pair of tear lines and each of the second regions extends across at least a portion of the respective tear line and is removeably fastened to the other panel. The undergarment further includes a pair of ear flaps formed in one of the panels under the pair of attachment members. Each ear flap extends to a portion of one of the pair of tear lines and is fixed to one of the attachment members. As the attachment members are opened, the pair of ear flaps will cause the pair of tear lines to break, thereby opening the undergarment.

DETAILED DESCRIPTION

Figure 1:
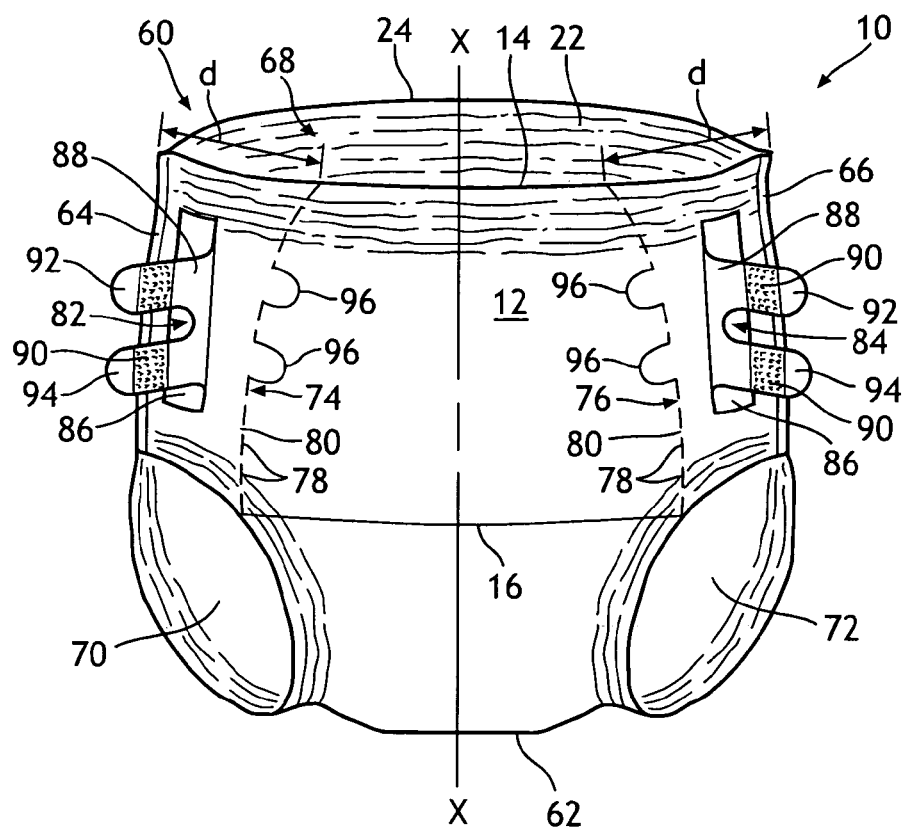
FIG. 1 is a perspective view of a refastenable pant-like disposable undergarment that includes a pair of ear flaps formed in the front panel such that each ear flap intersects one of the pair of tear lines.
Figure 2:
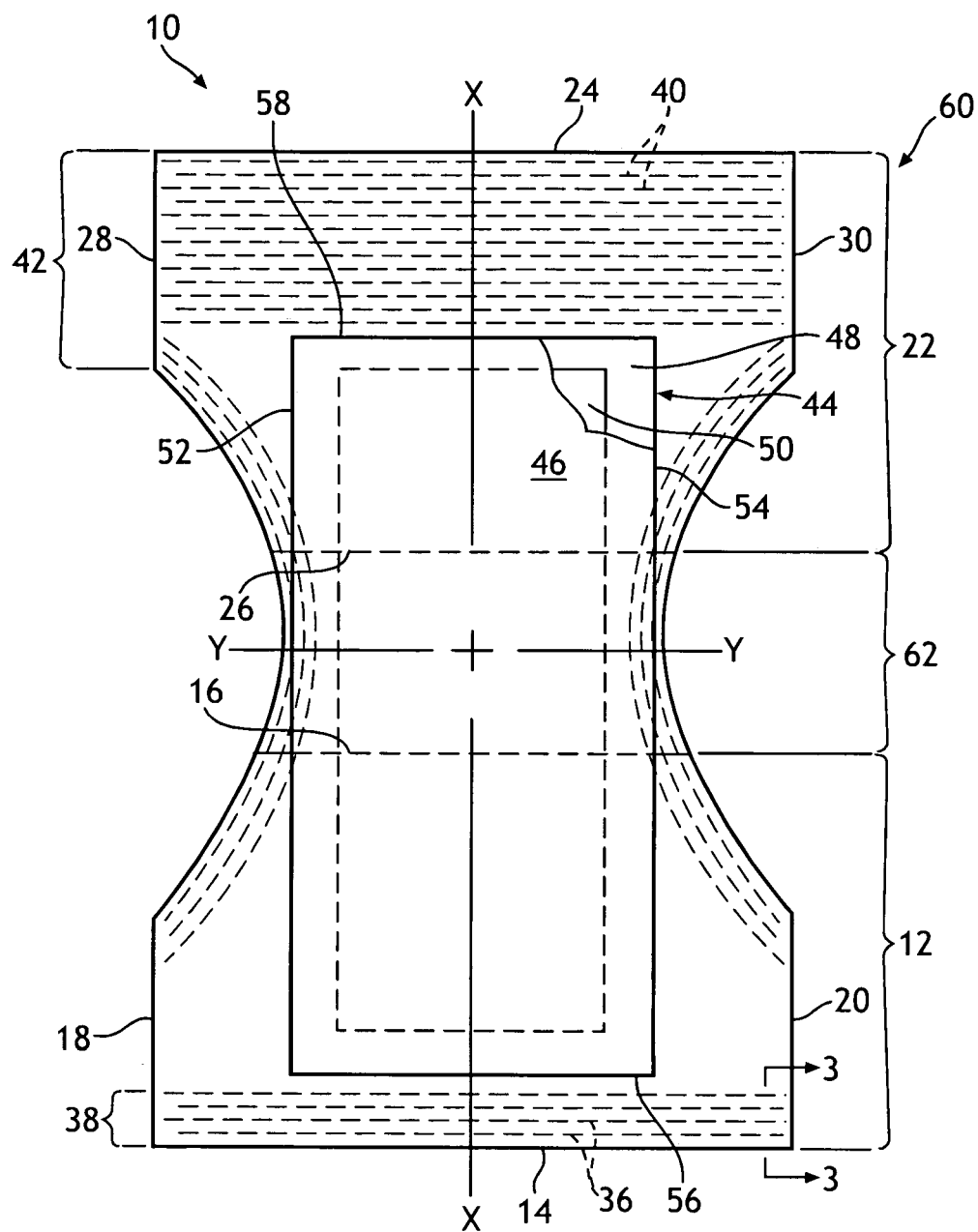
FIG. 2 is a plane view of the refastenable pant-like disposable undergarment before the front panel is secured to the back panel and shows the absorbent assembly secured to the front and back panels.

Referring to FIGS. 1 and 2, a refastenable pant-like disposable garment 10 for absorbing human discharge is shown. A "disposable garment" as used herein is an article that is intended to be worn by persons, including infants, toddlers or adults, which is designed for single use or temporary use and is meant to be disposed of after being used once instead of being laundered or dry cleaned for re-use. The refastenable pant-like disposable undergarment 10 is designed to absorb and/or retain one or more bodily discharges of waste material such as urine, perspiration, excrement, feces, menses, menstrual fluid, as well as other liquid and/or solid waste.

Figure 3:
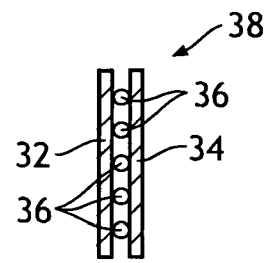
FIG. 3 is a cross-sectional view of FIG. 2 taken along line 3—3 showing a laminate structure with elastic strands sandwiched therebetween.

Referring to FIG. 2, the refastenable pant-like disposable undergarment 10 includes a front panel 12 having a first end 14, a second end 16, a first side 18, and a second side 20 and a back panel 22 having a first end 24, a second end 26, a first side 28, and a second side 30. The front and/or back panels, 12 and 22 respectively, can be formed from a single piece of material or they can be a laminate of two or more layers. The layers of the laminate can be of the same material or different material. In the cross-sectional view shown in FIG. 3, the laminate is depicted as being formed from a first layer 32 and a second layer 34. Sandwiched between the first and second layers, 32 and 34 respectively, are two or more strands of elastic 36. Desirably, two to ten strands of elastic 36 are utilized in the front panel 12 to form a front waist band 38. The elastic strands 36 can be formed from LYCRA®. LYCRA® is a registered trademark of E. I. Du Pont De Nemours & Co., having an office at 1007 Market Street, Wilmington, Del. 19898. The diameter and/or cross-sectional configuration of the elastic strands 36, the decitex (weight in grams per 10,000 meters of a strand) of the elastic strands 36, and tension imparted into the elastic strands 36 can all be varied to suit one's particular product needs. The back panel 22 normally contains more elastic strands than the front panel 12 to assure that the refastenable pant-like disposable undergarment 10 stays snug around the torso of the wearer. In FIG. 2, the back panel 22 is shown having from between about ten to about thirty strands of elastic 40 which form a back waist band 42. The elastic strands 40 can be formed from LYCRA® as well.

The front and/or back panels, 12 and 22 respectively, can be formed from a breathable or a non-breathable material. A polyolefin, such as polypropylene or polyethylene can be used as well as spunbond or a bonded carded web. A metallocene polypropylene works very well since it has a soft feel and can be easily ultrasonically bonded to itself.

Still referring to FIG. 2, the refastenable pant-like disposable undergarment 10 also includes an absorbent assembly 44. The absorbent assembly 44 includes a liquid pervious bodyside liner 46, a liquid-impervious outer cover 48, and an absorbent 50 positioned therebetween. The liquid pervious bodyside liner 46 is located nearest to the human body, adjacent to the skin of the user, and can be formed from a woven or non-woven material that will readily allow liquid or fluids to pass therethrough. The bodyside liner 46 is normally a very thin web that can be formed from natural or synthetic fibers, with or without apertures formed therein. A spunbond and a bonded carded web are two materials that work well as a bodyside liner 46. "Spunbond" is manufactured and sold commercially by Kimberly-Clark Corporation having an office at 401 North Lake Street, Neenah, Wis. 54956. The liquid-impervious outer cover 48 is located on the exterior of the refastenable pant-like disposable undergarment 10, away from the skin of the user. The liquid-impervious outer cover 48 is formed from a material which will restrict fluid from penetrating or passing therethrough so as to prevent the outer clothing of the wearer from becoming soiled. Desirably, the outer cover 48 has a soft feel so as not to chafe the inner thighs of the wearer. The outer cover 48 can also be formed from natural or synthetic fibers. The outer cover 48 can be formed from a material that is not noisy when squeezed or wrinkled so that the refastenable pant-like disposable undergarment 10 remains discreet. The outer cover 48 can also be formed from a breathable material. The outer cover 48 can further be formed from a laminate where one layer of the laminate is liquid-impervious. Examples of various materials that can be used as the outer cover 48 include a polyolefin, such as polypropylene or polyethylene; a liquid impervious layer bonded to a spunbond; and a thermoplastic material bonded to a spunbond. Other materials known to those skilled in the art can also be utilized.

The absorbent 50 is sealed within the liquid pervious bodyside liner 46 and the liquid-impervious outer cover 48. The absorbent 50 can be formed from natural or synthetic materials. The absorbent 50 can be made from cellulosic fibers, wood pulp, textile fibers or other absorbent materials known to those skilled in the art. Superabsorbents, in solid form and in the shape of small particles, granules, flakes, etc., can be mixed in with the absorbent material to increase the absorbent capacity of the absorbent 50.

The absorbent assembly 44 further includes a pair of side edges 52 and 54 and a pair of end edges 56 and 58. The absorbent assembly 44 is secured to the front panel 12 approximate the end edge 56 and is secured to the back panel 22 approximate the end edge 58. The absorbent assembly 44 can be secured to the front and back panels, 12 and 22 respectively, in a permanent fashion or in a removable fashion to enable a replacement assembly to be later substituted. The pair of end edges 56 and 58 can be secured to the front and back panels, 12 and 22 respectively, by any means known to those skilled in the art. Some examples of securement include the use of an adhesive, co-adhesives, glue, ultrasonics, stitching using thread, heat and/or pressure seals, mechanical means, etc. The exact distance the end edges 56 and 58 are spaced from the first ends, 14 and 24 respectively, of the front and back panels 12 and 22 can vary to optimize the functionality of the refastenable pant-like disposable undergarment 10. It should be noted that the distance the end edge 56 is spaced away from the first end 14 of the front panel 12 can be less than, equal to or greater than the distance that the end edge 58 is spaced away from the first end 24 of the back panel 22. For active adults, the absorbent assembly 44 may be positioned such that the end edges 56 and 58 are equally spaced from the first ends 14 and 24 of the front and back panels, 12 and 22 respectively. For a bedridden person, the absorbent assembly 44 can be positioned closer to the first end 24 of the back panel 22 so as to provide added protection against leakage of body fluid from a person lying in a recumbent manner. Desirably, for active adults wearing the refastenable pant-like disposable undergarment 10, the distance the end edge 56 of the absorbent assembly 44 is spaced away from the first end 14 of the front panel 12 is less than the distance that the end edge 58 of the absorbent assembly 44 is spaced away from the first end 24 of the back panel 22. This arrangement allows the absorbent assembly 44 to be skewed more towards the front of the refastenable pant-like disposable undergarment 10 and function better for both male and female users.

When the front panel 12, the back panel 22 and the absorbent assembly 44 are secured together, a chassis 60 is formed having a longitudinal central axis X—X and a transverse central axis Y—Y. A crotch panel 62 is located between the front panel 12 and the back panel 22. The front panel 12, the back panel 22 and the crotch panel 62 can be formed from one material or from two or three separate pieces of material. This chassis 60 can be folded along the transverse axis Y—Y such that the first and second sides, 18 and 20 respectively, of the front panel 12 are aligned approximate with the first and second sides, 28 and 30 respectively, of the back panel 22.

Referring again to FIG. 1, the front and back panels, 12 and 22 respectively, are folded and joined together by a pair of seams 64 and 66 to form a waist opening 68 and a pair of leg openings 70 and 72. The seams 64 and 66 can be aligned parallel to one another or they can be angled relative to one another. Desirably, the seams 64 and 66 are aligned parallel to one another and are aligned parallel to the longitudinal axis X—X of the chassis 60. Referring now to FIG. 2, portions of the side edges 52 and 54 of the absorbent assembly 44 are aligned adjacent to the leg openings, 70 and 72 respectively. Also portions of the end edges 56 and 58 of the absorbent assembly 44 are aligned adjacent to and spaced slightly away from the waist opening 68.

Still referring to FIG. 1, the refastenable pant-like disposable undergarment 10 also includes a pair of tear lines 74 and 76 formed in the front panel 12. The pair of tear lines 74 and 76 can be formed as perforation lines, separation points, score lines, lines of weakness, zones of weakness, breakaway lines or areas, chain stitching, etc. Chain stitching is a stitch formed in the material such that when an end of the stitching is pulled, the stitch unravels and the material separates. The tear lines 74 and 76 can be either linear or non-linear in shape. Non-linear shapes can include curved or arcuate profiles, a saw tooth profile, a zig-zag profile, a sinusoidal profile, or any other geometrical profile that is not a straight line. As shown in FIG. 1, the pair of tear lines 74 and 76 is depicted as a pair of perforation lines being curved or arcuate in configuration and each is arranged in a concave relationship to one another. Alignment in a convex relationship could be utilized, if desired. The pair of curved or arcuate shaped tear lines 74 and 76 is aligned non-parallel to the seams 64 and 66. This unique configuration makes for a more aesthetically pleasing garment and one that is ergonomically easier to open. Each of the tear lines 74 and 76 extends from the waist opening 68 to one of the respective leg openings 70 and 72. In addition, each of the tear lines 74 and 76 is tearable by applying a minimum amount of pressure onto the front panel 12.

When the pair of tear lines 74 and 76 are perforation lines, each line can consist of multiple land areas 78 aligned adjacent to open areas 80. The length of each of the land areas 78 can be less than, equal to, or be greater than the length of each of the open areas 80. The ratio between the length of a land to an open area, 78 and 80 respectively, can be adjusted to increase or decrease the amount of force required to break the pair of tear lines 74 and 76. The type of material into which the tear lines 74 and 76 are formed, the thickness of the material, the configuration of the tear lines 74 and 76, as well as other features, will all have an impact on the amount of force needed to break the tear lines 74 and 76. It should also be noted that the amount of force needed to start to break the tear lines 74 and 76 may be slightly greater than the amount of force needed to continue to tear open the tear lines 74 and 76.

The pair of tear lines 74 and 76 can be formed such that each of the land areas 78 has a length that is equal to the length of each of the open areas 80. Alternatively, the length of the land and/or open areas, 78 and 80 respectively, can vary along a portion of or over the total length of the tear lines 74 and 76. It has been found that when the length of the open areas 80 is greater than the length of the land areas 78, that the tear lines 74 and 76 can be easily broken. It is important to design the land and open areas, 78 and 80 respectively, such that the tear lines 74 and 76 are easy for the user to break yet ensure that the tear lines 74 and 76 will not break prematurely. Good results have been obtained by dimensioning the length of each of the open areas 80 to be at least two times greater than the length of each of the land areas 78. Desirably, the length of each of the open areas 80 will be at least three times greater than the length of each of the land areas 78. More desirably, the length of each of the open areas 80 will be at least four times greater than the length of each of the land areas 78.

Still referring to FIG. 1, each of the tear lines, 74 and 76 respectively, is shown being aligned non-parallel to one of the seams, 64 and 66 respectively. As depicted, the curved or arcuately shaped tear lines 74 and 76 are arranged convex to the seams 64 and 66, respectively. By "convex" it is meant that each of the tear lines 74 and 76 curve or bulge outward, as the exterior of a sphere, toward one of the adjacent seams 64 or 66. The radius of a curved or arcuately shaped tear line can vary. The exact radius will be partly dictated by the distance between the waist opening 68 and the respective leg opening 70 or 72. As shown in FIG. 1, the tear lines 74 and 76 form mirror images of one another.

Each of the pair of tear lines 74 and 76 extend downward from the waist opening 68 to one of the respective leg openings 70 and 72. The exact position where the tear lines 74 and 76 intersect the waist opening 68 and/or the respective leg openings 70 and 72 can vary. However, a sufficient distance (d) should be present between the points where the seam 64 and the tear line 74 intersect the waist opening 68, and between the points where the seam 66 and the tear line 76 intersect the waist opening 68. By moving the pair of tear lines 74 and 76 outward, away from the seams 64 and 66, it makes it easier for the wearer of the refastenable pant-like disposable undergarment 10 to visually see the tear lines 74 and 76 when he or she looks down at the front panel 12. The exact dimension for the distance (d) will vary depending on the size and shape of the refastenable pant-like disposable undergarment 10.

Figure 4:
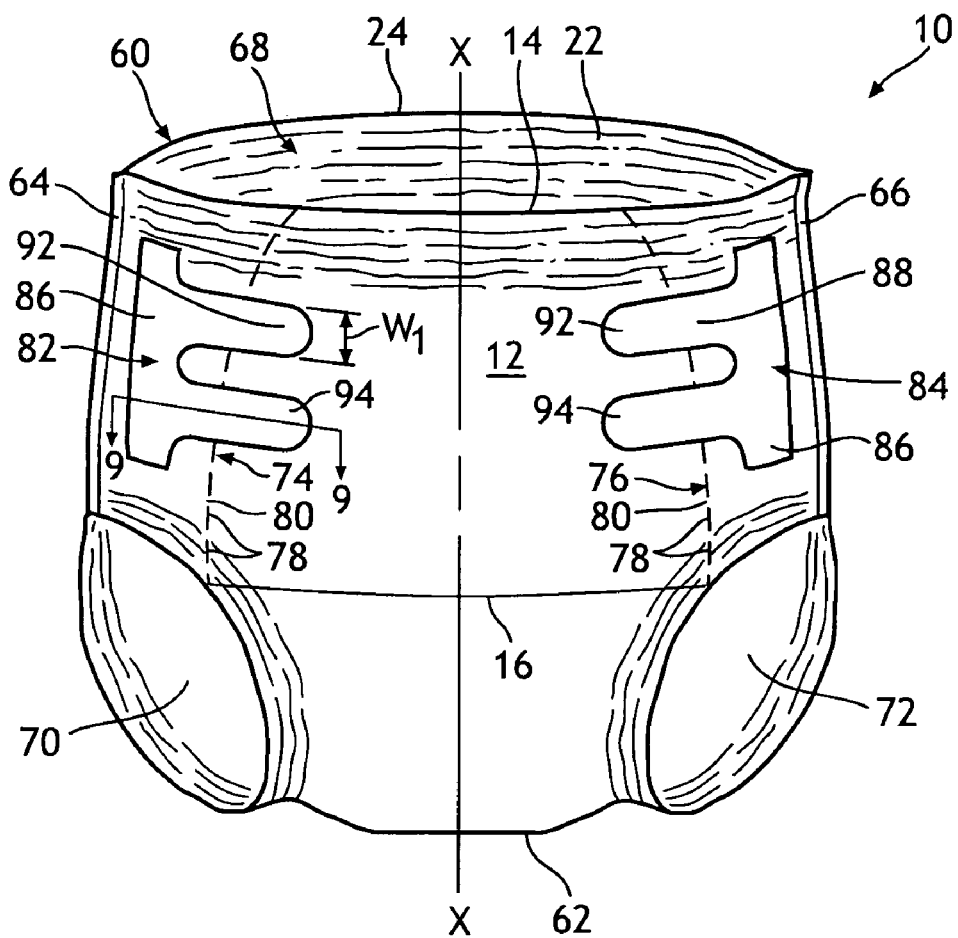
FIG. 4 is a perspective view of the refastenable pant-like disposable undergarment when the attachment members are fastened to the front panel and overlap the pair of ear flaps.

Referring to FIGS. 1 and 4, the refastenable pant-like disposable undergarment 10 further includes a pair of attachment members 82 and 84, each having a first region 86 and a second region 88. Each of the first regions 86 is secured to the front panel 12 on one side of each of the tear lines 74 and 76. The first regions 86 can be permanently attached to the front panel 12. By "permanently attached" is meant that the first regions 86 are secured to the front panel 12 and are not designed to be removable without destroying the bond or attachment mechanism. The attachment of the first regions 86 to the front panel 12 can be by an ultrasonic bond, by an adhesive, by glue, by a mechanical fastener such as thread or by other attachment means known to those skilled in the art. Each of the second regions 88 extend forward over a portion of the respective tear lines 74 and 76, see FIG. 4, and is removeably attached to the front panel 12. By "removeably attached" is meant that the second regions 88 can be fastened, unfastened and then refastened to the front panel 12 more than once. In FIG. 1, the second regions 88 are depicted as being unfastened and pulled back away from the front panel 12.

Desirably, the pair of attachment members 82 and 84 will cover from between about 25% to about 90% of each of the pair of tear lines 74 and 76. More desirably, the pair of attachment members 82 and 84 will cover from between about 30% to about 85% of each of the pair of tear lines 74 and 76. Most desirably, the pair of attachment members 82 and 84 will cover from between about 35% to about 80% of each of the pair of tear lines 74 and 76. This amount of coverage is important for it is desired that a portion of the pair of tear lines 74 and 76 be visually present to the user both before and during use of the refastenable pant-like disposable undergarment 10. In FIG. 4, one will notice that the shape and location of the tear lines 74 and 76 make them visible in the front panel 12 above, in the middle, as well as below the attachment members 82 and 84. The greater the amount of visibility of the tear lines 74 and 76 in the front panel 12, the better.

When the refastenable pant-like disposable undergarment 10 is an incontinent undergarment designed to be worn by older adults who may suffer from poor eye sight, dementia or possibly arthritis, it is best to make them consciously aware of the presence and location of the pair of tear lines 74 and 76. This will aid them in being able to break the tear lines 74 and 76. Also, when the user knows that the attachment members 82 and 84 can be released and reapplied both before, as well as after, the tear lines 74 and 76 are broken, it enables the user to keep their disposable undergarment 10 snug about their waist at all times.

Returning again to FIG. 1, the second regions 88 of each of the pair of attachment members 82 and 84 can be formed from a material that has hook-like properties or it can contain a piece of material 90 that has hook-like properties. In FIG. 1, a piece of hook material 90 is secured to the inside surface of the second regions 88 of the pair of attachment members 82 and 84. The hook material can be VELCRO® which is capable of engaging into the fibers of the material forming the outer cover 48, see FIG. 2. VELCRO® is a registered trademark of Velcro USA, Inc. having an office at 406 Brown Avenue, Manchester, N.H. 03103. In FIG. 1, the outer cover 48 would be considered to be a loop material.

Referring to FIGS. 1 and 4, the second regions 88 of the pair of attachment members 82 and 84 are depicted as having two finger tabs 92 and 94. It should be noted that a single larger tab can be used if desired. However, it has been found that when the front panel 12 has a length dimension or rise (measured parallel to the longitudinal axis X—X) that is greater than about six inches (about 15.24 cm), that two individual finger tabs 92 and 94 work better than a single larger tab. One reason for this is that the individual finger tabs 92 and 94 allow for different sections of the front panel 12 to be adjusted independent of the remaining sections. This ability to localize the area of adjustment creates a better fit of the refastenable pant-like disposable undergarment 10 to the torso of the user. For example, one can snug up the front panel 12 relative to one or both of the leg opening 70 and 72 without disturbing the fit around the waist opening 68. In addition, the non-parallel arrangement of the pair of tear lines 74 and 76 relative to the seams 64 and 66, especially when the tear lines 74 and 76 have a non-linear configuration, seems to fit the curvature of the torso better and thereby provides improved fit of the refastenable pant-like disposable undergarment 10.

Figures 5, 6, 7:
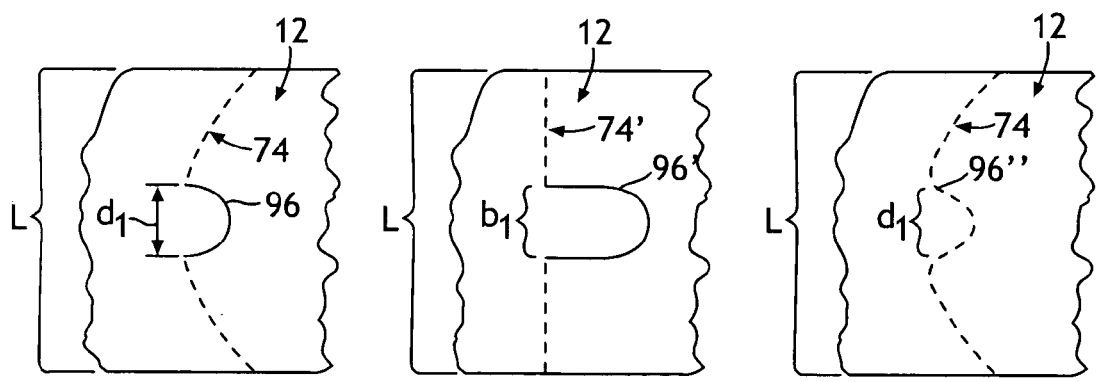
FIG. 5 is a schematic view of an ear flap having a semi-round configuration.
FIG. 6 is a schematic view of an ear flap having a tongue shape configuration.
FIG. 7 is a schematic view of a non-linear tear line and an ear flap formed by perforating the material from which it is formed.

Referring now to FIGS. 1 and 5, the refastenable pant-like disposable undergarment 10 also includes at least one pair of ear flaps 96 formed in or secured to the front panel 12. The pair of ear flaps 96 is aligned under the second region 88 of each of the pair of attachment members 82 and 84 when the second region 88 is fastened to the front panel 12. In FIG. 1, two pairs of ear flaps 96 are depicted in a spaced apart relationship. Therefore, there are two ear flaps 96 associated with each attachment member 82 and 84. It should be noted that multiple ear flaps 96 can be utilized, if desired. Desirably, the first pair of ear flaps 96 is spaced at least about 0.5 inches (about 1.2 mm) away from the second pair of ear flaps 96. The spacing is measured along the length of the respective tear line 74 or 76. More desirably, the first pair of ear flaps 96 is spaced at least about 1 inch (about 2.5 mm) away from the second pair of ear flaps 96. This spacing will allow the two pairs of ear flaps 96 to function properly as well as be aligned with the finger tabs, 92 and 94 respectively.

Each of the two pairs of ear flaps 96 is depicted as being formed from the material forming the front panel 12. Another way of stating this is to say that the ear flaps 96 are cut, severed, scored or perforated from the material that forms the front panel 12. Alternatively, the ear flaps 96 can be attached to, bonded or secured to the front panel 12 by an ultrasonic bond, an adhesive, a mechanical fastener or by some other means known to those skilled in the art. Each of the ear flaps 96 extends outward from one of the pair of tear lines 74 or 76 toward the longitudinal centerline X—X of the undergarment 10. The ear flaps 96 can be aligned to extend toward the seams 64 and 66 if the attachment members 82 and 84 are reversed 180 degrees, such that first region 86 is located closer to the longitudinal centerline X—X.

Still referring to FIGS. 1, 4 and 5, the actual shape of the ear flaps 96 can vary. In FIGS. 1 and 5, the two pairs of ear flaps 96 are shown having a semi-round shape. The semi-round portion of each of the ear flaps 96 is shown being completely severed from the front panel 12. The diameter $d_1$ or base side of the ear flap 96 remains connected to the front panel 12 and is not severed therefrom. The diameter $d_1$ or base side of each ear flap 96 is actually curved or arcuate in shape since it lies along the same arc as the curved or arcuate tear line 74. Desirably, the diameter $d_1$ or base side is coaxially aligned with one of the pair of tear lines 74 or 76. The diameter $d_1$ or base side of each of the ear flaps 96 acts as a hinge and enables the ear flap 96 to pivot and move outward away from the front panel 12. By "outward" it is meant that the ear flap 96 is capable of moving away from the torso of the wearer of the refastenable pant-like disposable undergarment 10. The diameter $d_1$ or base side of the ear flap 96 can be less than, equal to or greater in dimension than the width $w_1$ of each of the finger tabs, 92 and 94. In FIG. 4, the width of the finger tab 92 $w_1$ is greater than the diameter $d_1$ or base side of the ear flap 96. In this embodiment, the ear flaps 96 are not visible when the finger tabs 92 and 94 overlap them. Desirably, the diameter $d_1$ or base side of the ear flap 96 is equal to or smaller in dimension than the width $w_1$ of each of the finger tabs, 92 and 94. More desirably, the diameter $d_1$ or base side of the ear flap 96 is smaller in dimension than the width $w_1$ of each of the finger tabs, 92 and 94.

Still referring to FIG. 5, one will notice that the diameter $d_1$ or base side of the ear flap 96 is smaller in length than the overall length L of the curved or arcuately shaped tear line 74. The diameter $d_1$ or base side can be about 0.25 inches (about 0.63 mm) or greater in dimension. Desirably, the diameter $d_1$ or base side of each of the ear flaps 96 will extend at least about 5% along the length L of the tear line 74. More desirably, the diameter $d_1$ side of each of the ear flaps 96 will extend at least about 10% along the length L of the tear line 74. Most desirably, the diameter $d_1$ or base side of each of the ear flaps 96 will extend at least about 20% along the length L of the tear line 74.

It should be noted that in FIG. 5, only one ear flap 96 is shown and the overall profile of the ear flap 96 is not drawn to scale relative to the length of the tear line 74. The reason for this is to better show the ear flap 96.

Turning now to FIG. 6, an alternative embodiment for both the tear line 74 and the ear flap 96 is depicted. In FIG. 6, the tear line 74' is shown as being a straight or linear line and an ear flap 96' is shown as having a tongue-shaped profile. The tongue-shaped portion extends outward from the tear line 74' and is completely severed from the material forming the front panel 12. The ear flap 96' has a base side $b_1$ that is smaller than the overall length L of the tear line 74'. The base side $b_1$ can be about 0.25 inches (about 0.63 mm) or greater in length. The length of the tongue, measured perpendicular to the base side $b_1$, can be about 0.3 inches (about 0.75 mm) or longer. A dimension of between about 0.3 inches (about 0.63 mm) to about 1.5 inches (about 3.8 mm) works well for most adult incontinent undergarments. Desirably, the base side $b_1$ of the ear flap 96' will extend at least about 5% along the length L of the tear line 74'. More desirably, the base side $b_1$ of the ear flap 96' will extend at least about 10% along the length L of the tear line 74'. Most desirably, the base side $b_1$ of the ear flap 96' will extend at least about 20% along the length L of the tear line 74'. The base side $b_1$ of the ear flap 96' remains connected to the front panel 12 and is not severed therefrom. The base side $b_1$ of the ear flap 96' is straight or linear since the tear line 74' is linear. Desirably, the base side $b_1$ of the ear flap 96' is coaxially aligned with one of the pair of tear lines 74 or 76. The base side $b_1$ acts as a hinge and enables the ear flap 96' to pivot and move outward away from the front panel 12. By "outward" it is meant that the ear flap 96' is capable of moving away from the torso of the wearer of the refastenable pant-like disposable undergarment 10.

Referring now to FIG. 7, still another embodiment of the ear flap 96 is depicted. In FIG. 7, the tear line 74 again has a curved or arcuate shape and the ear flap 96" has a semi-round shape. The ear flap 96" again extends outward from the tear line 74. It should be noted that in this embodiment, as well as in the previous two embodiments, that the ear flaps 96, 96' and 96" could extend a short distance to the other side of the respective tear lines 74, 74' or 74, if desired.

In FIG. 7, the semi-round ear flap 96" differs from the embodiment shown in FIG. 5 in that its semi-round portion is formed by perforations formed into the front panel 12. The perforations function to at least partially sever the semi-round portion from the front panel 12. The perforations can be similar or different in size and shape to those forming the perforations in the tear line 74. In this embodiment, the semi-round portion of the ear flap 96" is not completely severed from the front panel 12 while the diameter $d_1$ or base side of the ear flap 96" remains connected to the front panel 12 and is not severed therefrom. The diameter $d_1$ or base side of the ear flap 96" is actually curved or arcuate in shape since it lies along the same arc as the tear line 74. Desirably, the diameter $d_1$ or base side of the ear flap 96" is coaxially aligned with the tear line 74. As explained above, the diameter $d_1$ or base side acts as a hinge and enables the ear flap 96" to pivot and move outward away from the front panel 12. By "outward" it is meant that the ear flap 96" is capable of moving away from the torso of the wearer of the refastenable pant-like disposable undergarment 10.

Figure 8:
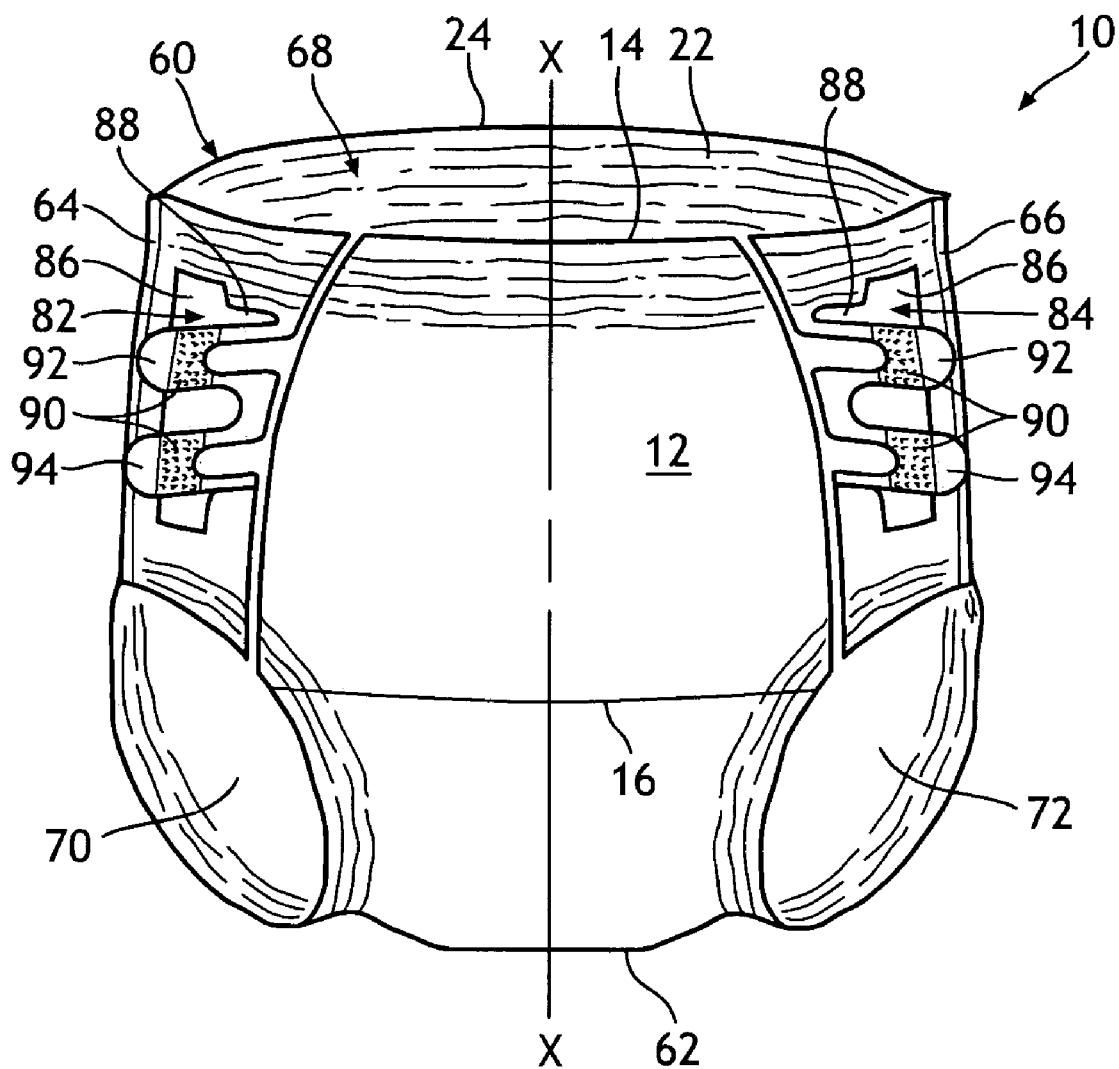
FIG. 8 is a perspective view of the refastenable pant-like disposable undergarment showing the opening of the attachment members with the ear flaps secured thereto which causes the pair of tear lines to break.

Referring again to FIGS. 1, 4 and 8, the ear flaps 96, 96' and 96" all function in the same way to assist in breaking the tear lines 74 and 76 and allowing the refastenable pant-like undergarment 10 to be opened. The refastenable pant-like disposable undergarment 10 is manufactured and sold in the configuration depicted in FIG. 4. The refastenable pant-like undergarment 10 can be pulled up around a user's torso like regular cloth underwear or it can first be opened by pulling back the attachment members 82 and 84, see FIG. 1, and then breaking the pair of tear lines 74 and 76. Assuming that the refastenable pant-like undergarment 10 is pulled up around the user's torso and the wearer wants to check to see the condition of the absorbent assembly 44, he or she would pull back the attachment members 82 and 84. In doing so, the second region 88 of each of the pair of attachment members 82 and 84 is unfastened from the front panel 12. The piece of hook material 90 located on the underside of each of the finger tabs 92 and 94 will cause the ear flaps 96 to remain attached as the finger tabs 92 and 94 are pulled back and separated from the front panel 12. As the finger tabs 92 and 94 are separated from the front panel 12, the diameter $d_1$ or base side $b_1$ of each of the ear flaps 96, 96' and 96" will be pulled back and upward away from the pair of tear lines 74 and 76. This action will cause the pair of tear lines 74 and 76 to break. Further upward and backward pulling of the finger tabs 92 and 94 away from the longitudinal centerline X—X will cause the pair of tear lines 74 and 76 to completely sever, see FIG. 8, thereby opening the refastenable pant-like disposable undergarment 10.

The refastenable pant-like disposable undergarment 10 can be closed or refastened after being inspected by the wearer by simply again securing the attachment members 82 and 84 to the front panel 12. This action will allow the finger tabs 92 and 94 to bridge across the openings where the pair of tear lines 74 and 76 was located. The hook material 90, located on the lower or bottom side of the finger tabs 92 and 94, will again adhere to the outer surface of the front panel 12 and the refastenable pant-like disposable undergarment 10 will be closed. The hook material 90 is of sufficient strength to retain the refastenable pant-like disposable undergarment 10 in a closed configuration. In the closed position, the refastenable pant-like disposable undergarment 10 will snugly fit around the wearer's torso.

Figure 9:
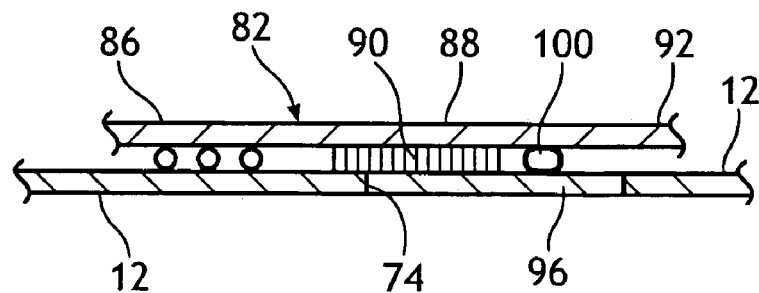
FIG. 9 is a cross-sectional view of FIG. 4 taken along line 9—9 showing the ear flap secured to the attachment member.

Referring now to FIG. 9, a cross-sectional view of the attachment member 82 secured to the front panel 12 is shown wherein the finger tab 92 completely covers and overlies the ear flap 96. Sometimes it is advantageous to secure each of the ear flaps 96 to the underside or lower surface of one of the finger tabs 92 or 94. This securement will assure that the ear flap 96 will move in conjunction with the respective finger tab 92 or 94 as the finger tabs 92 or 94 are pulled up and back away from the front panel 12. In FIG. 9, the ear flap 96 is secured to the lower or bottom surface of the finger tab 92 by a bond 100. The bond 100 can be an adhesive bond, an ultrasonic bond, a hook and loop bond, a mechanical bond, a chemical bond or any other form of bond known to those skilled in the art. The bond 100 functions to permanently secure the ear flap 96 to the finger tab 92 such that as the finger tab 92 is pulled back away from the longitudinal centerline X—X of the refastenable pant-like disposable undergarment 10, the ear flap 96 will remain connected thereto.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A refastenable pant-like disposable undergarment comprising:
   a) a front panel;
   b) a back panel;
   c) an absorbent assembly secured to said front and back panels, and said front and back panels being joined together by a pair of seams to form a waist opening and a pair of leg openings;
   d) a pair of tear lines formed in said front panel with each extending from said waist opening to one of said respective leg openings;
   e) a pair of attachment members each having a first region and a second region, each of said first regions being secured to one side of one of each tear line and each of said second regions extending across and being removeably fastened to said other side of said respective tear line; and
   f) a pair of ear flaps aligned under said pair of attachment members, each ear flap extending outward from a portion of one of said tear lines, and as each of said second regions of said pair of attachment members is unfastened, said pair of ear flaps will remain attached thereto and cause said pair of tear lines to break.

2. The refastenable pant-like disposable undergarment of claim 1 wherein each of said ear flaps has a tongue shape.

3. The refastenable pant-like disposable undergarment of claim 1 wherein each of said ear flaps has a semi-round shape.

4. The refastenable pant-like disposable undergarment of claim 3 wherein each of said ear flaps has an arcuate side.

5. The refastenable pant-like disposable undergarment of claim 4 wherein said arcuate side is coaxially aligned with one of said pair of tear lines.

6. The refastenable pant-like disposable undergarment of claim 1 wherein said ear flap has a semi-round portion that is at least partially severed from said front panel.

7. The refastenable pant-like disposable undergarment of claim 1 wherein there are two ear flaps associated with each attachment member.

8. The refastenable pant-like disposable undergarment of claim 7 wherein said two ear flaps are spaced apart from one another by at least about 0.5 inches.

9. The refastenable pant-like disposable undergarment of claim 1 wherein each of said pair of ear flaps extend a distance of at least about 5% along the length of one of said tear lines.

10. A refastenable pant-like disposable undergarment comprising:
   a) a front panel;
   b) a back panel;
   c) an absorbent assembly secured to said front and back panels, and said front and back panels being joined together by a pair of seams to form a waist opening and a pair of leg openings;
   d) a pair of non-linear tear lines formed in said front panel, each of said pair of tear lines extending from said waist opening to one of said respective leg openings;
   e) a pair of attachment members each having a first region and a second region, each of said first regions being secured to one side of each tear line and each of said second regions extending across and being removeably fastened to said other side of said respective tear line; and
   f) a pair of ear flaps formed in said front panel and aligned under said pair of attachment members, each ear flap being bonded to one of said attachment members and each ear flap extending outward from one of said tear lines, and as each of said second regions of said pair of attachment members is unfastened, said pair of ear flaps will remain attached thereto and cause said pair of tear lines to break.

11. The refastenable pant-like disposable undergarment of claim 10 wherein each of said pair of ear flaps has a portion that is at least partially severed from said front panel.

12. The refastenable pant-like disposable undergarment of claim 10 wherein each of said ear flaps has a base side that is larger in dimension than the width of each finger tab that overlaps it.

13. The refastenable pant-like disposable undergarment of claim 10 wherein each of said pair of ear flaps is secured to said attachment member by an ultrasonic bond.

14. The refastenable pant-like disposable undergarment of claim 10 wherein each of said pair of ear flaps is secured to said attachment member by an adhesive.

15. The refastenable pant-like disposable undergarment of claim 10 wherein each of said pair of ear flaps has an arcuate side that is coaxially aligned with one of said pair of tear lines, and said arcuate side has a length of at least 0.25 inches.

16. A refastenable pant-like disposable undergarment comprising:
   a) a front panel;
   b) a back panel;
   c) an absorbent assembly secured to said front and back panels, and said front and back panels being joined together by a pair of seams to form a waist opening and a pair of leg openings;
   d) a pair of arcuate tear lines formed in said front panel, each of said pair of tear lines extending from said waist opening to one of said respective leg openings;
   e) a pair of attachment members each having a first region and a second region, each of said first regions being permanently secured to said front panel and each of said second regions extending across one of said pair of tear lines and being removeably fastened to said front panel; and
   f) a pair of ear flaps secured to said front panel and aligned under said pair of attachment members, each ear flap extending outward from one of said tear lines, and as each of said second regions of said pair of attachment members is unfastened, said pair of ear flaps will remain attached thereto and cause said pair of tear lines to break.

17. The refastenable pant-like disposable undergarment of claim 16 wherein each of said ear flaps has a semi-round portion.

18. The refastenable pant-like disposable undergarment of claim 16 wherein each of said ear flaps has a portion that is at least partially severed from said front panel.

19. The refastenable pant-like disposable undergarment of claim 16 wherein each of said ear flaps has a base side that is smaller in dimension than the width of each finger tab that overlaps it.

20. The refastenable pant-like disposable undergarment of claim 16 wherein each of said ear flaps has a base side that is equal in dimension to the width of each finger tab that overlaps it.

* * * * *